US 8,442,622 B2

(12) United States Patent
Wang

(10) Patent No.: US 8,442,622 B2
(45) Date of Patent: May 14, 2013

(54) VERTEBRA SEGMENTATION APPARATUS, VERTEBRA SEGMENTATION METHOD, AND RECORDING MEDIUM WITH PROGRAM FOR VERTEBRA SEGMENTATION

(75) Inventor: Caihua Wang, Tokyo (JP)

(73) Assignee: Fujifilm Corporation, Tokyo (JP)

( * ) Notice: Subject to any disclaimer, the term of this patent is extended or adjusted under 35 U.S.C. 154(b) by 161 days.

(21) Appl. No.: 12/954,697

(22) Filed: Nov. 26, 2010

(65) Prior Publication Data
US 2011/0130653 A1 Jun. 2, 2011

(30) Foreign Application Priority Data

Nov. 27, 2009 (JP) ................................. 2009-270837
Aug. 31, 2010 (JP) ................................. 2010-194795

(51) Int. Cl.
*A61B 5/00* (2006.01)
(52) U.S. Cl.
USPC ........... 600/427; 600/407; 600/425; 382/128; 382/131
(58) Field of Classification Search .................. 600/407, 600/424, 425, 427; 382/128, 131
See application file for complete search history.

(56) References Cited

U.S. PATENT DOCUMENTS

| 7,561,728 | B2 * | 7/2009 | Abufadel et al. ............. 382/132 |
| 7,804,986 | B2 * | 9/2010 | Lai et al. .................. 382/128 |
| 2009/0169087 | A1 | 7/2009 | Doi et al. |
| 2009/0262998 | A1 | 10/2009 | Wang et al. |

FOREIGN PATENT DOCUMENTS

| JP | 2004-313478 | 11/2004 |
| JP | 2006-102508 | 4/2006 |
| JP | 2008-093254 | 4/2008 |
| JP | 2009-207727 | 9/2009 |
| JP | 2009-531129 | 9/2009 |
| JP | 2009-254600 | 11/2009 |

OTHER PUBLICATIONS

Masahiro et al., "Quantitative Evaluation of Osteoporosis Likelihood using Multi-slice CT Images", the Institute of Electronics, Information and Communication Engineers Technical Report MI2005-90, pp. 97-100, Jan. 2006.
Yao et al., "Automated Spinal Column Extraction and Partitioning"., In 3rd IEEE International Symposium on Biomedical Imaging, pp. 390-393 (2006).
Weiss, K.L. et al., Automated Spine Survey Iterative Scan Technique, Radiology, Apr. 2006, vol. 239, No. 1, pp. 255-262.

(Continued)

*Primary Examiner* — Unsu Jung
*Assistant Examiner* — Amanda Lauritzen
(74) *Attorney, Agent, or Firm* — Young & Thompson

(57) ABSTRACT

Based on generated tomographic images, a first feature quantity representative of a clearness of sectional shapes crossing the Z' axis at the vertebrae is calculated for each of respective points on the Z' axis. Further, based on the generated tomographic images, a second feature quantity representative of a clearness of sectional shapes parallel to the Z' axis at the vertebrae is calculated for each of the respective points on the Z' axis. A third feature quantity representative of a regularity of an array of the vertebrae is calculated for each of the respective points on the Z' axis, based on the calculated first feature quantity and the calculated second feature quantity. Positions of the vertebrae on the Z' axis are calculated based on the third feature quantity, which is calculated for each of respective points on the Z' axis.

11 Claims, 12 Drawing Sheets

OTHER PUBLICATIONS

Tanaka, Takaaki et al., Quantitative Evaluation of Osteoporosis Likelihood Using Multi-slice CT Images, The Institute of Electronics Information and Communication Engineers, IEICE Technical Report MI2007-136(Jan. 2008), pp. 401-404, with English Abstract.

Notice of Allowance dated Jan. 31, 2012 issued by the Japanese Patent Office for corresponding Japanese Patent Application No. 2010-194795.

* cited by examiner

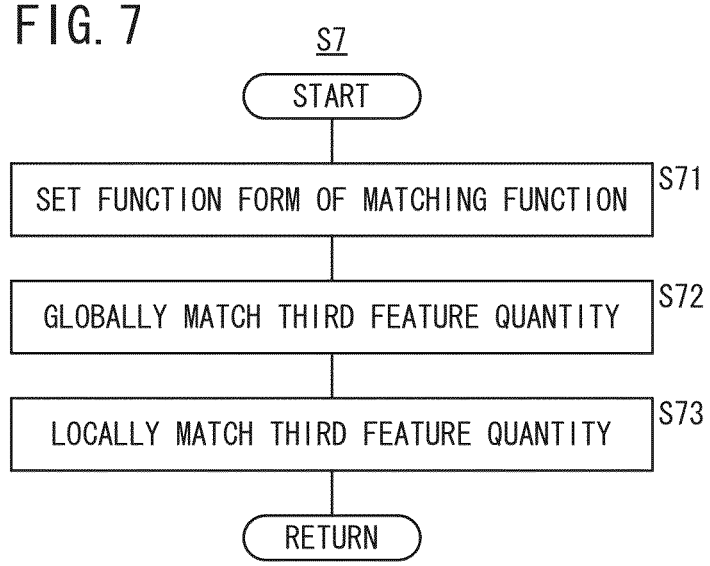

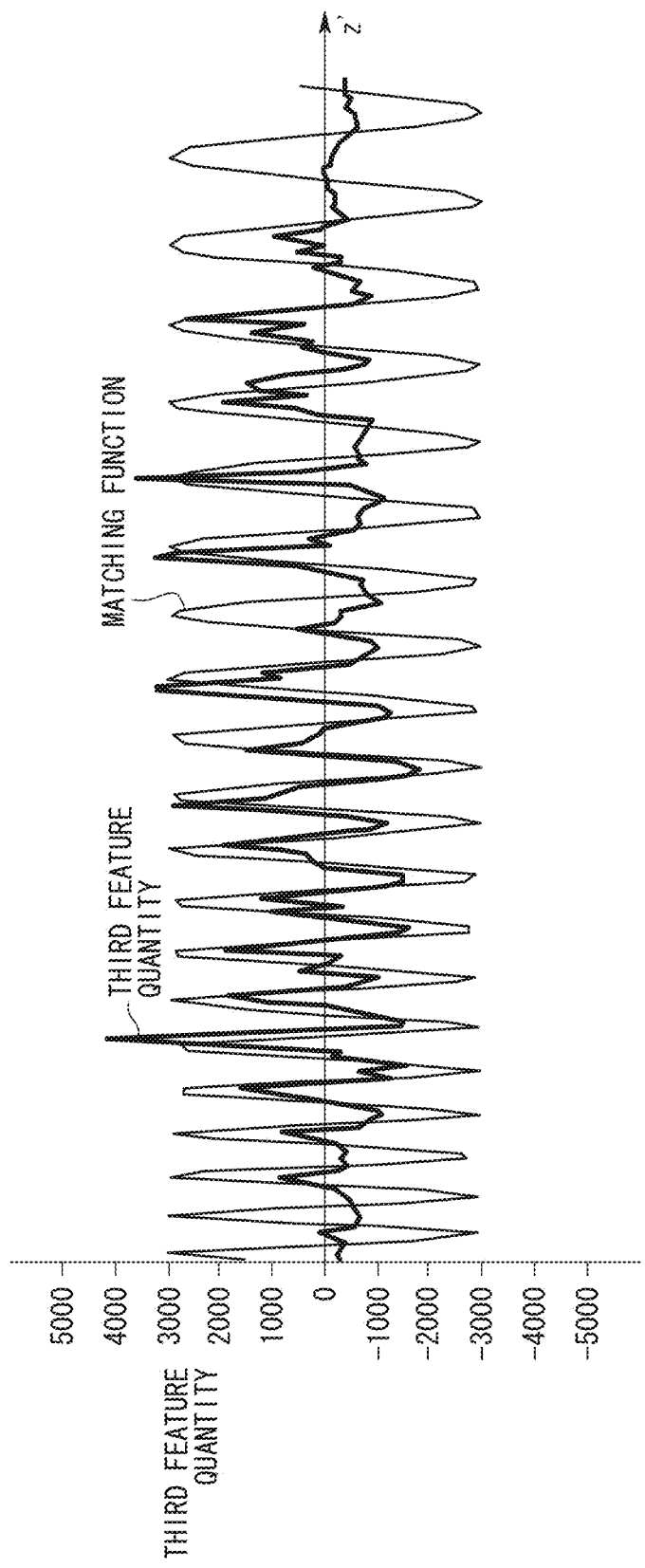

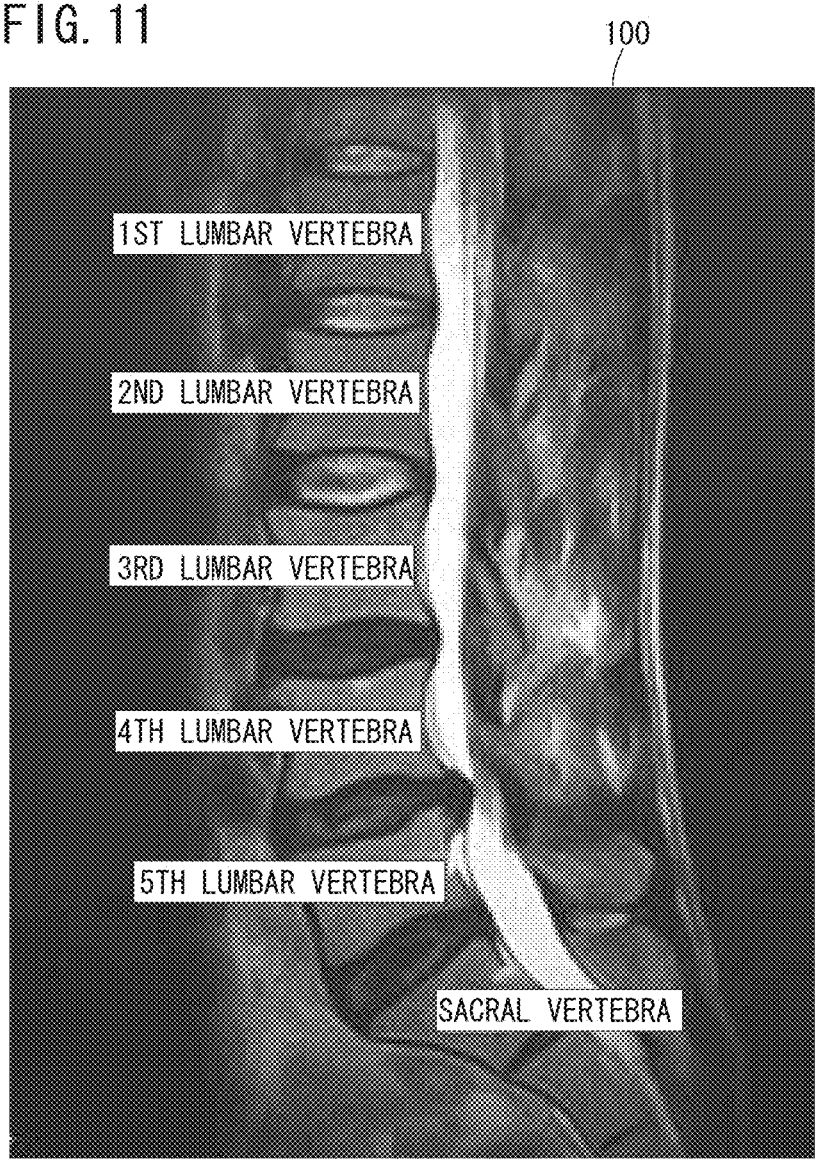

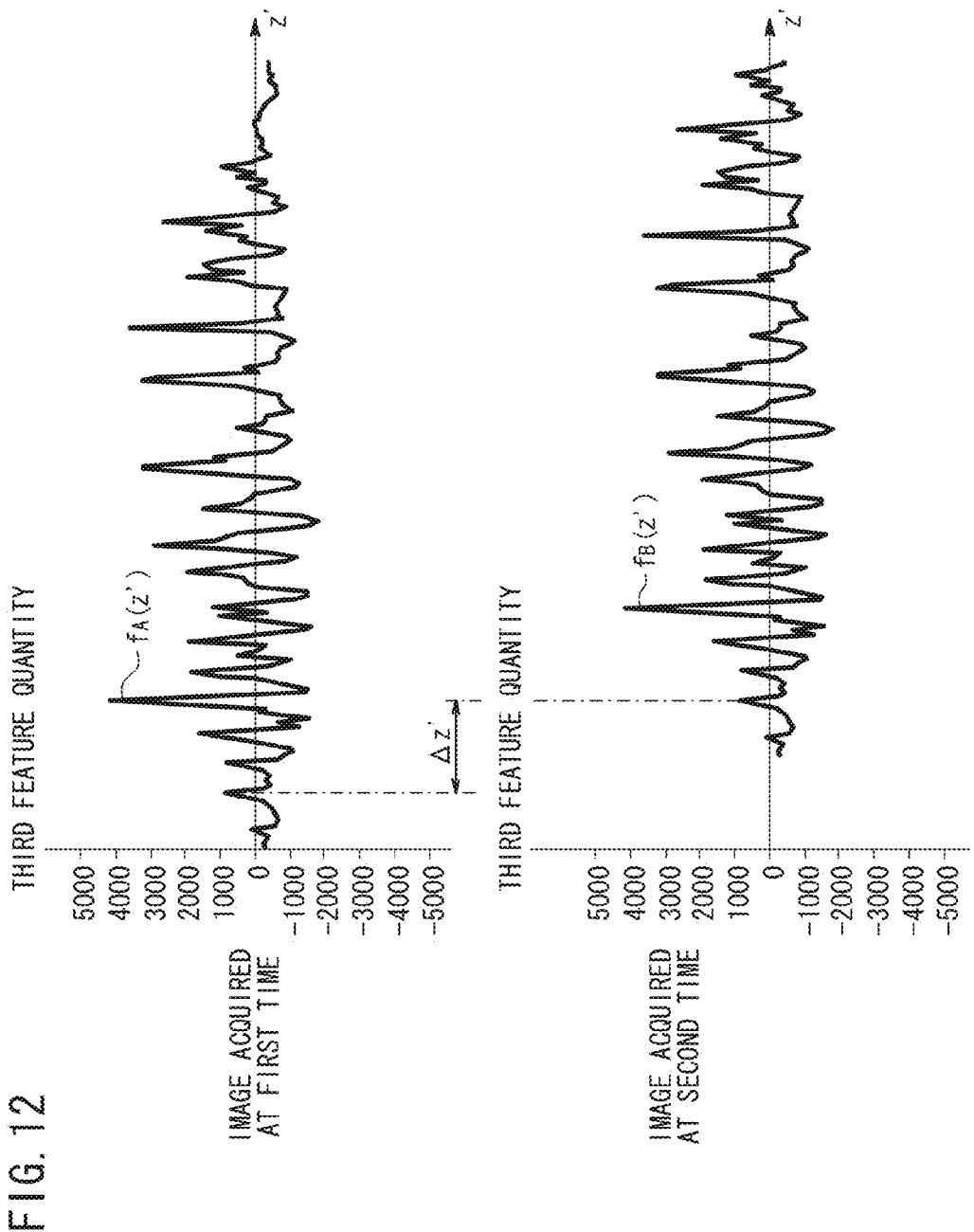

VERTEBRA SEGMENTATION APPARATUS, VERTEBRA SEGMENTATION METHOD, AND RECORDING MEDIUM WITH PROGRAM FOR VERTEBRA SEGMENTATION

CROSS-REFERENCE TO RELATED APPLICATION

This application is based upon and claims the benefit of priority from Japanese Patent Applications No. 2009-270837 filed on Nov. 27, 2009 and No. 2010-194795 filed on Aug. 31, 2010, of which the contents are incorporated herein by reference.

BACKGROUND OF THE INVENTION

1. Field of the Invention

The present invention relates to a vertebra segmentation apparatus, a vertebra segmentation method, and a recording medium storing a program for partitioning and recognizing a plurality of vertebrae from a three-dimensional medical image that includes such vertebrae.

2. Description of the Related Art

Heretofore, there have been proposed in the medical field a variety of image processing algorithms for partitioning and recognizing a plurality of vertebrae based on tomographic images generated by scanning a subject from a chest region to the legs at a plurality of sectional positions. Such an image processing sequence is referred to as "vertebra segmentation".

"Quantitative Evaluation of Osteoporosis Likelihood using Multi-slice CT Images," the Institute of Electronics, Information and Communication Engineers Technical Report MI2005-90, pp. 97-100, January 2006, discloses a method of partitioning and recognizing vertebrae by estimating reference positions of respective intervertebral disc regions based on an average density profile along a spinal central line, and thereafter extracting vertebral body endplates and intervertebral discs according to an appropriate morphological process performed on tomographic images near such reference positions.

"Automated Spine Column Extraction and Partition," In 3rd IEEE International Symposium on Biomedical Imaging, pp. 390-393 (2006) discloses a method of partitioning and recognizing vertebrae by generating sagittal and coronal CRP (Curved Planar Reformation) images along a spinal central line, and extracting intervertebral discs based on a density value integral profile of tomographic images to which the spinal central line is normal.

It is generally known that if slices are thick in the scanning direction, i.e., the direction of the body axis, then the spatial resolution along the direction of the body axis becomes insufficient due to a partial volume effect, resulting in a reduction in the image rendering capability. It is particularly difficult to render intervertebral discs and vertebral body endplates separately on tomographic images within a range from the cervical vertebrae to the upper thoracic vertebrae, where each of the vertebrae is relatively short. As a result, the ability to detect intervertebral discs (i.e., the positional accuracy at which each vertebra is partition and recognized) is lowered.

As disclosed in Japanese Laid-Open Patent Publication No. 2009-207727, the inventor of the present invention has invented a method of estimating the position of a vertebral body by detecting a central line of a vertebra, then calculating a feature quantity representative of a density gradient in the direction of the body axis near the central line, specifying the central position of a vertebral body based on the feature quantity, and thereafter estimating the position of an intervertebral disc. According to this method, since the position of the intervertebral disc is estimated based on a vertebral cavernous region (hollow vertebral region), which is more detectable than the intervertebral disc, the positional accuracy at which each vertebra is partition and recognized is increased.

As disclosed in Japanese Laid-Open Patent Publication No. 2008-093254, the inventor of the present invention also has invented a display method of adding given mark images to corresponding locations on a plurality of different types of tomographic images, e.g., a combination of sagittal and coronal images, when the tomographic images are displayed adjacent to each other. Such a display method allows the user to accurately spot the position of a focus, for example.

SUMMARY OF THE INVENTION

An object of the present invention is to provide a vertebra segmentation apparatus, a vertebra segmentation method, and a recording medium storing a program, which have been invented in relation to the methods disclosed in Japanese Laid-Open Patent Publication No. 2009-207727 and Japanese Laid-Open Patent Publication No. 2008-093254, for partitioning and recognizing a plurality of vertebrae from a three-dimensional medical image of a subject whose spinal shape is deformed entirely or locally.

According to an aspect of the present invention, there is provided a vertebra segmentation apparatus comprising an image generator for generating tomographic images at intervals along central axes of respective vertebrae, a first feature quantity calculator for calculating a first feature quantity representative of a clearness of sectional shapes crossing the central axis at the vertebrae, for each of respective points on the central axis, based on the tomographic images generated by the image generator, a second feature quantity calculator for calculating a second feature quantity representative of a clearness of sectional shapes parallel to the central axis at the vertebrae, for each of the respective points on the central axis, based on the tomographic images generated by the image generator, a third feature quantity calculator for calculating a third feature quantity representative of a regularity of an array of the vertebrae, for each of the respective points on the central axis based on the first feature quantity calculated by the first feature quantity calculator and the second feature quantity calculated by the second feature quantity calculator, and a vertebral position estimator for estimating positions of the vertebrae on the central axis based on the third feature quantity, which is calculated by the third feature quantity calculator, for each of the respective points on the central axis.

The third feature quantity is calculated in view of cross-sectional shapes that are transverse and parallel to the central axis of each of the vertebrae. Accordingly, it is possible to perform a quantitative density analysis based on cross-sectional shapes from two different directions, thereby allowing the vertebrae to be partitioned and recognized in a three-dimensional medical image of the subject whose spinal shape is deformed entirely or locally. This process is particularly effective in analyzing a medical image of a spine, which is deformed in its entirety due to spinal curvature.

Preferably, the first feature quantity comprises a feature quantity for extracting an annular pattern around each of the respective points on the central axis. Thus, the cross-sectional shape, i.e., the annular pattern, crossing the central axis of each of the vertebrae, which has a substantially tubular cortex, can be quantized appropriately.

Preferably, the second feature quantity comprises a feature quantity for extracting a tubular pattern extending along the central axis. Thus, the cross-sectional shape, i.e., the tubular pattern, parallel to the central axis of each of the vertebrae, which has a substantially tubular cortex, can be quantized appropriately.

Preferably, the vertebra segmentation apparatus further comprises a function matcher for matching the third feature quantity calculated for each of the respective points on the central axis to a prescribed periodic function or a quasi-periodic function, wherein the vertebral position estimator estimates the positions of the vertebrae on the central axis based on the prescribed periodic function or the quasi-periodic function matched by the function matcher. Since the third feature quantity representative of the regularity of the array of the vertebrae is matched to a prescribed regular function form, high spatial frequency noise which is possessed by the third feature quantity can be reduced, for thereby estimating positions of the vertebrae with high accuracy.

Preferably, the prescribed periodic function or the quasi-periodic function includes a phase as a variable. In this case, the vertebra segmentation apparatus further comprises a phase determiner for determining the phase successively for the points on the central axis. It is thus possible to reduce an error in matching the third feature quantity to the matching function, for thereby estimating the position of each vertebra with high accuracy. This process is particularly effective in analyzing a medical image of a spine, which is deformed locally due to a bone fracture.

Preferably, the vertebra segmentation apparatus further comprises an identifying information allocator for allocating predefined identifying information to each of the vertebrae depending on the position thereof on the central axis, which is estimated by the vertebral position estimator.

Preferably, the identifying information allocator allocates identifying information, which is the same as the identifying information allocated based on the tomographic image generated at a first time, to each of the vertebrae depending on the position thereof on the central axis, which is estimated based on the tomographic image generated at a second time.

Preferably, the vertebra segmentation apparatus further comprises a feature quantity determiner for determining whether or not characteristics of the third feature quantity calculated based on the tomographic image generated at the first time agree with characteristics of the third feature quantity calculated based on the tomographic image generated at the second time, wherein the identifying information allocator allocates the identifying information, which is the same as the first-mentioned identifying information, if the feature quantity determiner judges that the characteristics of the third feature quantities agree with each other.

The identifying information preferably represents anatomical types of the vertebrae.

According to another aspect of the present invention, there is also provided a vertebra segmentation method comprising the steps of generating tomographic images at intervals along central axes of respective vertebrae, calculating a first feature quantity representative of a clearness of sectional shapes crossing the central axis at the vertebrae, for each of respective points on the central axis, based on the generated tomographic images, calculating a second feature quantity representative of a clearness of sectional shapes parallel to the central axis at the vertebrae, for each of the respective points on the central axis, based on the generated tomographic images, calculating a third feature quantity representative of a regularity of an array of the vertebrae, for each of the respective points on the central axis, based on the calculated first feature quantity and the calculated second feature quantity, and estimating positions of the vertebrae on the central axis based on the third feature quantity, which is calculated for each of the respective points on the central axis.

According to still another aspect of the present invention, there is further provided a recording medium storing therein a program for enabling a computer to perform a process of partitioning and recognizing a plurality of vertebrae from a three-dimensional medical image that includes the vertebrae, the program enabling the computer to function as an image generator for generating tomographic images at intervals along central axes of respective vertebrae, a first feature quantity calculator for calculating a first feature quantity representative of a clearness of sectional shapes crossing the central axis at the vertebrae, for each of respective points on the central axis, based on the generated tomographic images, a second feature quantity calculator for calculating a second feature quantity representative of a clearness of sectional shapes parallel to the central axis at the vertebrae, for each of the respective points on the central axis, based on the generated tomographic images, a third feature quantity calculator for calculating a third feature quantity representative of a regularity of the array of an vertebrae, for each of the respective points on the central axis, based on the calculated first feature quantity and the calculated second feature quantity, and a vertebral position estimator for estimating positions of the vertebrae on the central axis based on the third feature quantity, which is calculated for each of the respective points on the central axis.

With the vertebra segmentation apparatus, the vertebra segmentation method, and the recording medium storing the program according to the present invention, tomographic images are generated at intervals along the central axis of each of respective vertebrae, and based on the generated tomographic images, a first feature quantity representative of a clearness of sectional shapes crossing the central axis at the vertebrae is calculated for each of respective points on the central axis. Further, based on the generated tomographic images, a second feature quantity representative of a clearness of sectional shapes parallel to the central axis at the vertebrae is calculated for each of the respective points on the central axis. A third feature quantity representative of a regularity of an array of the vertebrae is calculated for each of the respective points on the central axis based on the calculated first feature quantity and the calculated second feature quantity. Positions of the vertebrae on the central axis are calculated based on the third feature quantity, which is calculated for each of the respective points on the central axis. Accordingly, it is possible to perform a quantitative density analysis based on cross-sectional shapes as viewed from two different directions, thereby allowing the vertebrae to be partitioned and recognized as a three-dimensional medical image of a subject whose spinal shape is deformed entirely or locally. Such a process is particularly effective in analyzing a medical image of a spine, which is deformed in its entirety due to spinal curvature.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 7 is a flowchart of a process for matching the third feature quantity to a prescribed function;

FIG. 8 is a graph showing the matched result of the third feature quantity;

FIG. 11 is a view showing an example of a sagittal tomographic image of lumbar vertebrae; and FIG. 12 is a set of graphs showing a specific process for checking a profile calculated at a first time and a profile calculated at a second time against each other.

DESCRIPTION OF THE PREFERRED EMBODIMENTS

A vertebra segmentation method according to a preferred embodiment of the present invention, and a vertebra segmentation apparatus for carrying out the vertebra segmentation method will be described in detail below with reference to the drawings.

Figure 1:
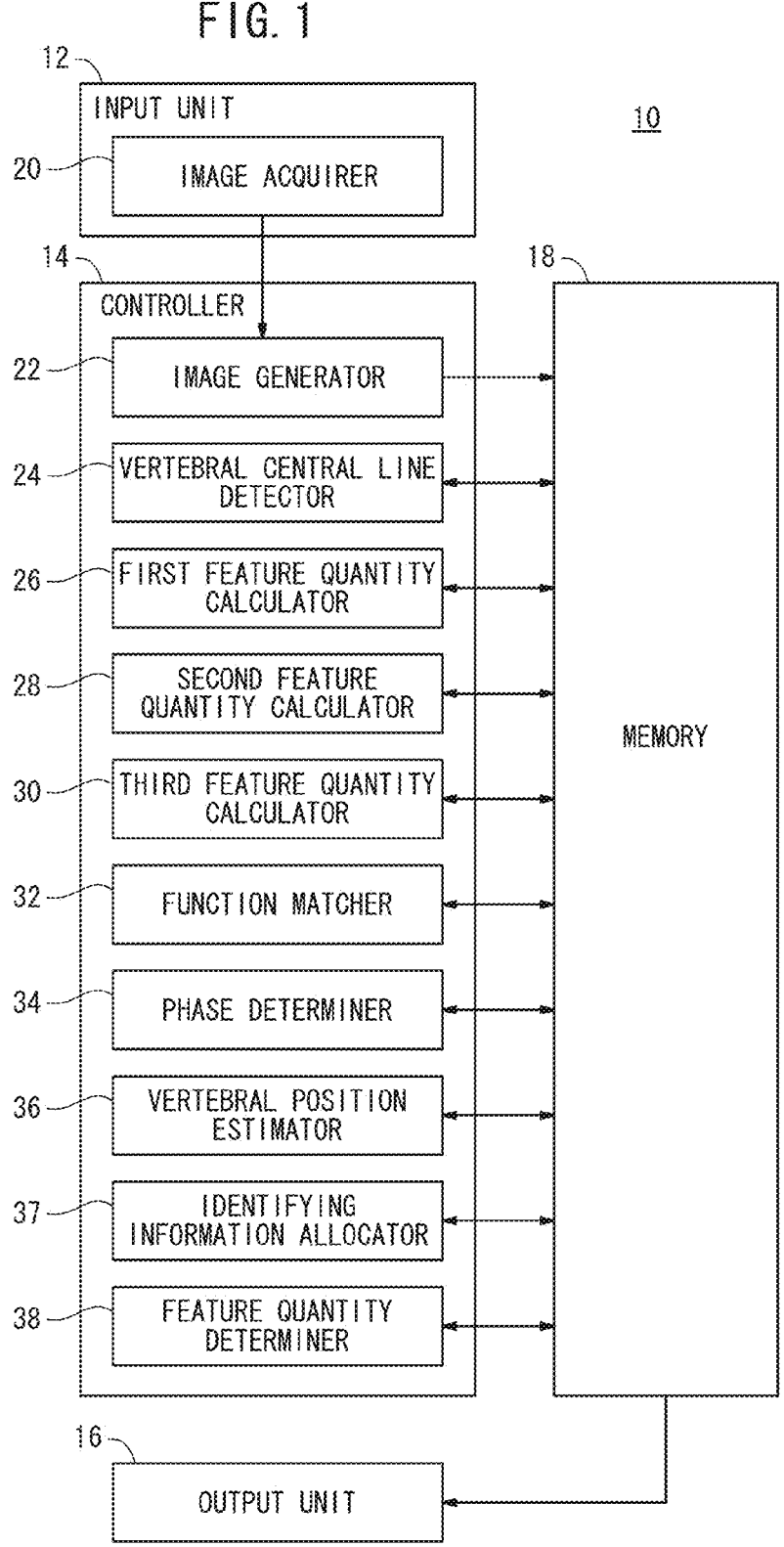
FIG. 1 is an electric block diagram of a vertebra segmentation apparatus according to an embodiment of the present invention.

FIG. 1 is an electric block diagram of a vertebra segmentation apparatus 10 according to an embodiment of the present invention. As shown in FIG. 1, the vertebra segmentation apparatus 10 comprises an input unit 12, a controller 14 that serves as an information processor such as a CPU or the like, an output unit 16, and a memory 18 that serves as a recording medium. The memory 18 stores a program for carrying out functions of the vertebra segmentation apparatus 10. The input unit 12 receives signals from external circuits. The input unit 12 includes an image acquirer 20 for acquiring a three-dimensional medical image, which includes a plurality of vertebrae. The image acquirer 20 may acquire not only a medical image, such as a CT image, an MRI image, an RI image, a PET image, or an X-ray image, but also a three-dimensional image, an artificially generated three-dimensional medical image, or a two-dimensional or three-dimensional medical image.

The controller 14 includes an image generator 22, a vertebral central line detector 24, a first feature quantity calculator 26, a second feature quantity calculator 28, a third feature quantity calculator 30, a function matcher 32, a phase determiner 34, a vertebral position estimator 36, an identifying information allocator 37, and a feature quantity determiner 38.

The image generator 22 generates a plurality of first tomographic images, e.g., axial tomographic images, along a given axial direction, e.g., a body axis direction, based on a three-dimensional medical image including a plurality of vertebrae, which has been acquired by the image acquirer 20. The image generator 22 records the generated first tomographic images in the memory 18. When the image acquirer 20 has directly acquired a plurality of first tomographic images representing axial cross sections of a three-dimensional medical image including a plurality of vertebrae, then the image generator 22 acquires the first tomographic images from the image acquirer 20 and records the first tomographic images in an unprocessed condition in the memory 18.

The image generator 22 also generates a plurality of second tomographic images along central axes of vertebrae, to be described later, based on the three-dimensional medical image acquired by the image acquirer 20. The image generator 22 can change the range of the generated image space area.

The vertebral central line detector 24 detects the central lines of vertebrae that are included in the first tomographic images generated by the image generator 22.

Figure 2:
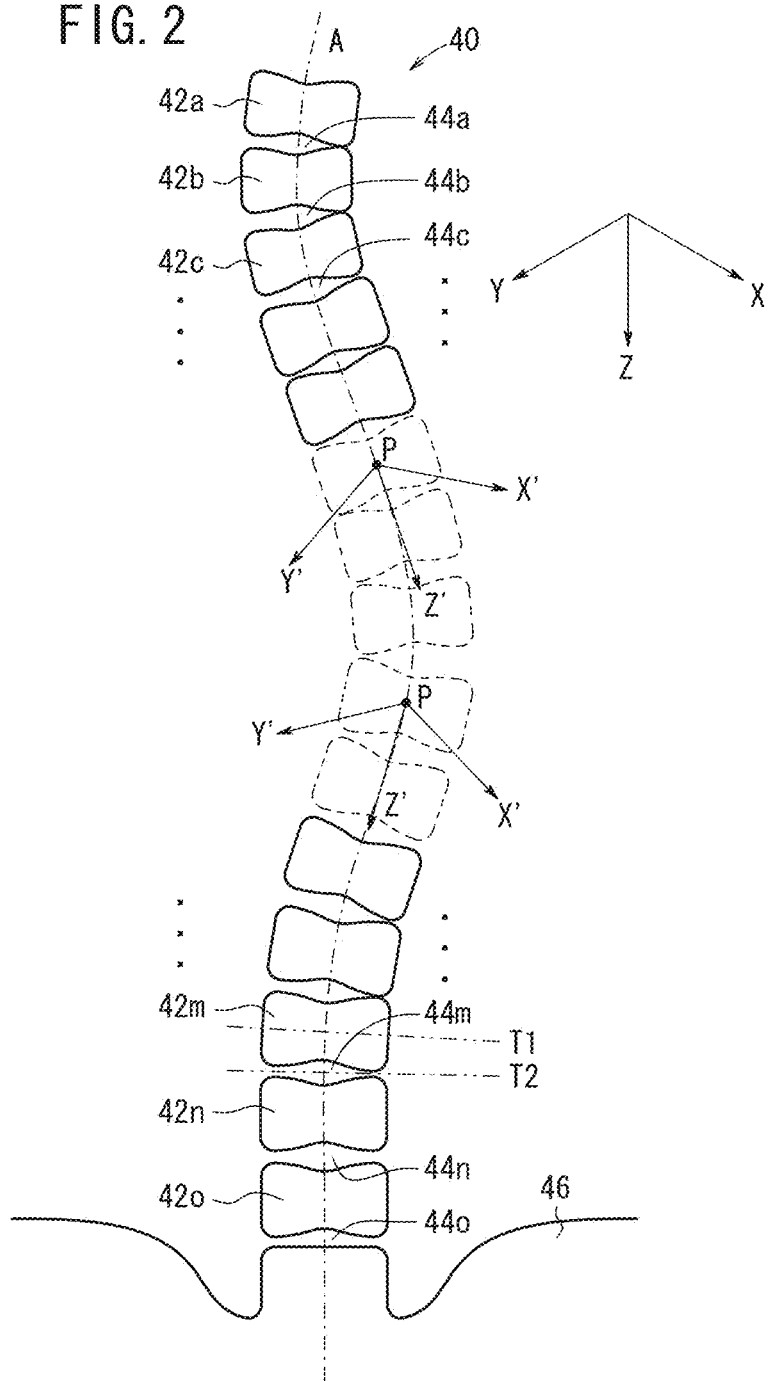
FIG. 2 is a schematic diagram of vertebrae, respective central lines of which are detected by a vertebral central line detector.

FIG. 2 schematically shows a sagittal image of an array of vertebrae. As shown in FIG. 2, a vertebral group 40 comprises fifteen respective vertebrae 42 each having a substantially tubular cortex. The vertebrae 42 are arranged with a curvature, which curves in an S shape with respect to the body axis (Z-axis) direction. Each of the vertebrae 42 is arranged along an S-shaped central line A of the vertebral group 40. A coordinate axis along the S-shaped central line A will hereinafter be referred to as a "Z'-axis".

The vertebral group 40 also includes a plurality of intervertebral discs 44 each interposed between two adjacent ones of the vertebrae 42. For illustrative purposes, in FIG. 2, the intervertebral discs 44 are not shown as discs, but as gaps between the vertebrae 42.

In order to distinguish between the vertebrae 42 and between the intervertebral discs 44, reference numerals thereof are combined with a suffix, represented by alphabetical letters "a" through "o". More specifically, the vertebrae 42 are denoted by 42a through 42o, and the intervertebral discs 44 are denoted by 44a through 44o, successively from the above. The lowermost intervertebral disc 44o has a lower surface thereof joined to the pelvis 46.

It requires an extremely sophisticated image processing technology to directly detect the central line A of each vertebra 42 using the first tomographic images. Alternatively, various detecting processes may be used to detect the central line A of each vertebra 42 based on structural features of the vertebra 42. For example, the central line A of each vertebra 42 can accurately be detected based on the relative positional relationship between the vertebra 42 and a spinal cord (not shown), the central line of which has been determined, which can relatively easily be detected by means of an image processing sequence (for details, see Japanese Laid-Open Patent Publication No. 2009-207727).

The central line of the spinal cord may be detected by a template matching method, a demarcation method, or a learning method based on AdaBoost, which is an algorithm for integrated machine learning.

The first feature quantity calculator 26 calculates a first feature quantity representative of a clearness of sectional shapes crossing the Z'-axes at the vertebrae 42 (see FIG. 2). The first feature quantity may be, for example, a feature quantity for extracting annular patterns around points P on the Z'-axes. The first feature quantity is calculated using an eigenvalue analysis of Hessian matrixes, to be described later. The first feature quantity calculator 26 records the calculated first feature quantity in the memory 18.

The second feature quantity calculator 28 calculates a second feature quantity representative of a clearness of sectional shapes parallel to the Z'-axes at the vertebrae 42 (see FIG. 2). The second feature quantity may be, for example, a feature quantity for extracting tubular patterns disposed around points P on the Z'-axes, and which extend along the Z'-axes. The second feature quantity is calculated using an eigenvalue analysis of Hessian matrixes, to be described later. The second feature quantity calculator 28 records the calculated second feature quantity in the memory 18.

The third feature quantity calculator 30 calculates a third feature quantity representative of a regularity of an array of the vertebrae 42. The third feature quantity may be represented by a weighted sum of the first and second feature quantities. The third feature quantity calculator 30 records the calculated third feature quantity in the memory 18.

The function matcher 32 matches the third feature quantity calculated for each of the points on the Z'-axes to a prescribed matching function (periodic function or quasi-periodic function). The term "periodic function" refers to a function, which is periodic with respect to positions represented by Z'-axis coordinates, and has a constant period irrespective of such positions. The term "quasi-periodic function" refers to a function, which is periodic with respect to positions represented by Z'-axis coordinates, and has a variable period dependent on such positions. The function matcher 32 records various constants for identifying the function form of the matching function in the memory 18.

The phase determiner 34 determines the value of a phase included as a variable in the function matched by the function matcher 32. The phase determiner 34 determines the value of a phase for each of respective points on the Z'-axes according to a dynamic programming process, for example. The phase determiner 34 records the determined phase in the memory 18.

The vertebral position estimator 36 estimates positions of respective vertebrae 42 in an XYZ coordinate system based on the third feature quantity. More specifically, the vertebral position estimator 36 estimates positions of the respective vertebrae 42 on the Z'-axes from the matching function, which is determined by the function matcher 32 and the phase determiner 34, and converts the estimated positions into positions in the XYZ coordinate system. The vertebral position estimator 36 records the estimated positions of the respective vertebrae 42 in the memory 18.

The identifying information allocator 37 allocates predefined identifying information to the vertebrae 42, the positions of which have been estimated in the XYZ coordinate system or on the Z'-axes. The identifying information may comprise various information representative of a relative positional relationship between the tomographic images, or various information representative of an absolute positional relationship in the structure of the subject. Various information representative of an absolute positional relationship includes anatomical types of vertebrae 42, as shall be described later.

The feature quantity determiner 38 checks characteristics (profiles with respect to the Z'-axes) of the third feature quantity calculated by the third feature quantity calculator 30 at a first time t1 and a second time t2, and determines whether or not such checked characteristics agree with each other. The feature quantity determiner 38 detects how the profiles are shifted from each other according to various algorithms, and calculates shift quantities Δz'.

The output unit 16 outputs positions of the vertebrae 42, which are estimated by the vertebral position estimator 36, to an external circuit. The output unit 16 may determine in advance reference positions at a plurality of locations, e.g., end points or central positions of the vertebrae 42 or the intervertebral discs 44, and may output such reference positions. The output unit 16 may output, together with positional information of the vertebrae 42, identifying information allocated by the identifying information allocator 37.

Operations of the vertebra segmentation apparatus 10 will be described below with reference to the flowchart shown in FIG. 3.

First, in step S1, the image generator 22 generates X-Y tomographic images at intervals along the direction of the body axis (Z-axis), i.e., a plurality of first tomographic images, based on a three-dimensional medical image including a plurality of vertebrae 42, which is acquired by the image acquirer 20.

If the image acquirer 20 has directly acquired a plurality of first tomographic images representing axial cross sections, then the image generator 22 acquires the first tomographic images acquired by the image acquirer 20.

Then, in step S2, the vertebral central line detector 24 detects central lines A of the vertebrae 42, which are included in the first tomographic images generated or acquired in step S1. The vertebral central line detector 24 detects central lines A of the vertebrae 42 according to the detecting process described above. Thereafter, the central lines A are established as new coordinate axes (Z'-axes).

Then, in step S3, the image generator 22 generates X'-Y' tomographic images at intervals along the central lines A (Z'-axes) detected in step S3, i.e., a plurality of second tomographic images, based on the three-dimensional medical image acquired by the image acquirer 20. The image generator 22 may generate a plurality of second tomographic images using only image information that can be reconstructed within a region around the Z'-axes, which covers the area where the vertebral group 40 exists, rather than using all of the image information that makes up the acquired three-dimensional medical image, so that the memory space used by the memory 18 can be reduced and the processing time of the controller 14 can be shortened.

Then, in step S4, the first feature quantity calculator 26 calculates a first feature quantity from the second tomographic images generated in step S3. The first feature quantity is expressed by the following equation (1):

$$f_1(z') = \int\int_{(x',y',z') \in R} \frac{\lambda_1(x', y', z')}{|\lambda_2(x', y', z')| + |\lambda_3(x', y', z')| + \varepsilon} \quad (1)$$

$$|\vec{E}_1(x', y', z') \cdot \vec{d}| dx' dy'$$

where (x', y', z') represents the position in the XYZ coordinate system, and R represents an integral region indicative of cortex regions of the vertebrae 42 in the second tomographic images.

Inherent values and inherent vectors in a 3×3 Hessian matrix are represented respectively by $(\lambda_1, \lambda_2, \lambda_3)$ and $(E_1, E_2, E_3)$. The inherent values are related to each other by $\lambda_1 \leq \lambda_2 \leq \lambda_3$. In equation (1), d represents a vector directed from a point (0, 0, z') toward (x', y', z') on a Z'-axis, which is represented by d=(x', y', 0), and ε represents a minute positive integer provided to prevent division by zero.

Figure 4A:
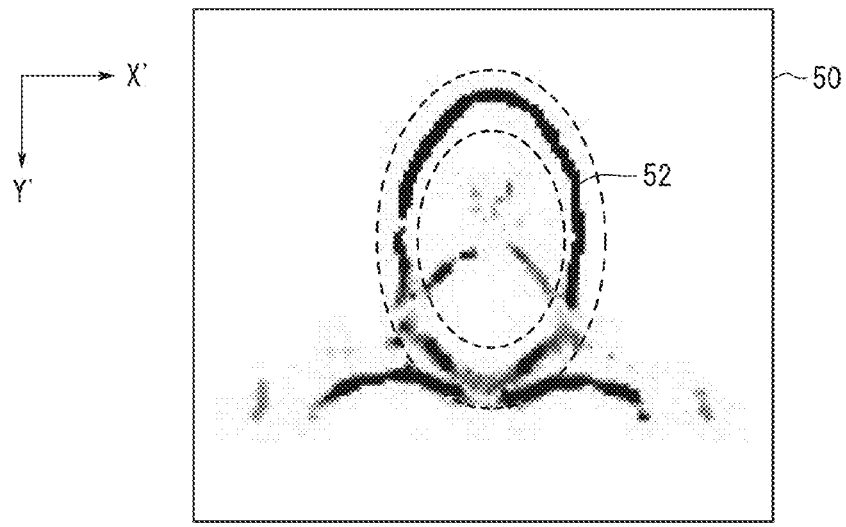
FIGS. 4A and 4B are diagrams showing two-dimensional distributions of first feature quantities (integrands) at respective sectional positions.
Figure 4B:
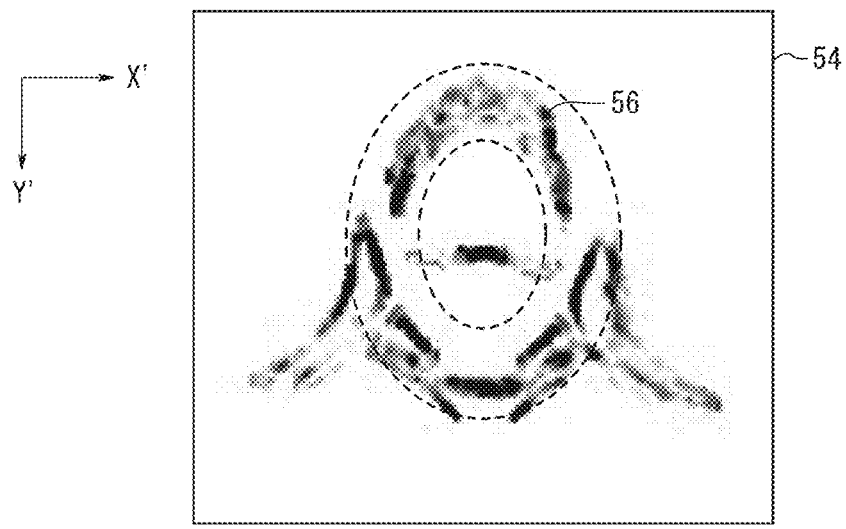

FIGS. 4A and 4B are diagrams showing two-dimensional distributions of the first feature quantity (integrands) at respective sectional positions. In FIGS. 4A and 4B, numerical values of the first feature quantity (integrands) on the second tomographic images are made visual by way of image shading. The first feature quantity is displayed such that the density is higher at positions with larger first feature quantities, whereas the density is lower at positions with smaller first feature quantities.

FIG. 4A shows a visual image 50 indicating a calculated value of a first feature quantity at a sectional position T1 (see FIG. 2). Since the sectional position T1 represents the middle position of the vertebra 42m, the second tomographic image thereof includes a cross-sectional shape of the cortex of the vertebra 42m. Therefore, the visual image 50 clearly shows an annular black pattern 52. As a result, the first feature quantity, which represents a sum of integrands within the integral region R, is large.

FIG. 4B shows a visual image 54 indicating the calculated value of a first feature quantity at a sectional position T2 (see FIG. 2). Since the sectional position T2 represents a position of the intervertebral disc 44m, the second tomographic image thereof does not include a cross-sectional shape of the cortex of any vertebra, but includes the edge of the intervertebral disc 44m. The visual image 54 exhibits a slight annular pale pattern 56. As a result, the first feature quantity, which represents the sum of integrands within the integral region R, is small.

According to another calculating process, the first feature quantity calculator 26 may calculate a first feature quantity using a Laplacian filter (second-order differential filter), for detecting the intensity of an edge. Alternatively, the first feature quantity calculator 26 may calculate a first feature quantity using a Laplacian of Gaussian filter (hereinafter referred to as "LoG filter"), for weighting and smoothing pixels within a local region according to a Gaussian distribution, and then applying a Laplacian filter to detect zero-crossing points as an edge.

Then, in step S5, the second feature quantity calculator 28 calculates a second feature quantity from the second tomographic images generated in step S3. The second feature quantity is expressed by the following equation (2):

$$f_2(z') = \int\int_{(x',y',z') \in c} \frac{\lambda_1(x', y', z')}{|\lambda_2(x', y', z')| + |\lambda_3(x', y', z')| + \varepsilon} \quad (2)$$

$$|\vec{E}_1(x', y', z') \cdot \vec{e}_z| dx' dy'$$

where (x', y', z') represents a position in an X'Y'Z' coordinate system, and C represents a region around the central axis A (Z'-axis).

As with equation (1), inherent values and inherent vectors in a 3×3 Hessian matrix are represented respectively by ($\lambda_1$, $\lambda_2$, $\lambda_3$) and ($E_1$, $E_2$, $E_3$). The inherent values are related to each other by $\lambda_1 \leq \lambda_2 \leq \lambda_3$. In equation (2), $e_z$ represents a unit vector (0, 0, 1) on the Z'-axis, and $\varepsilon$ represents a minute positive integer provided to prevent division by zero.

Figure 5:
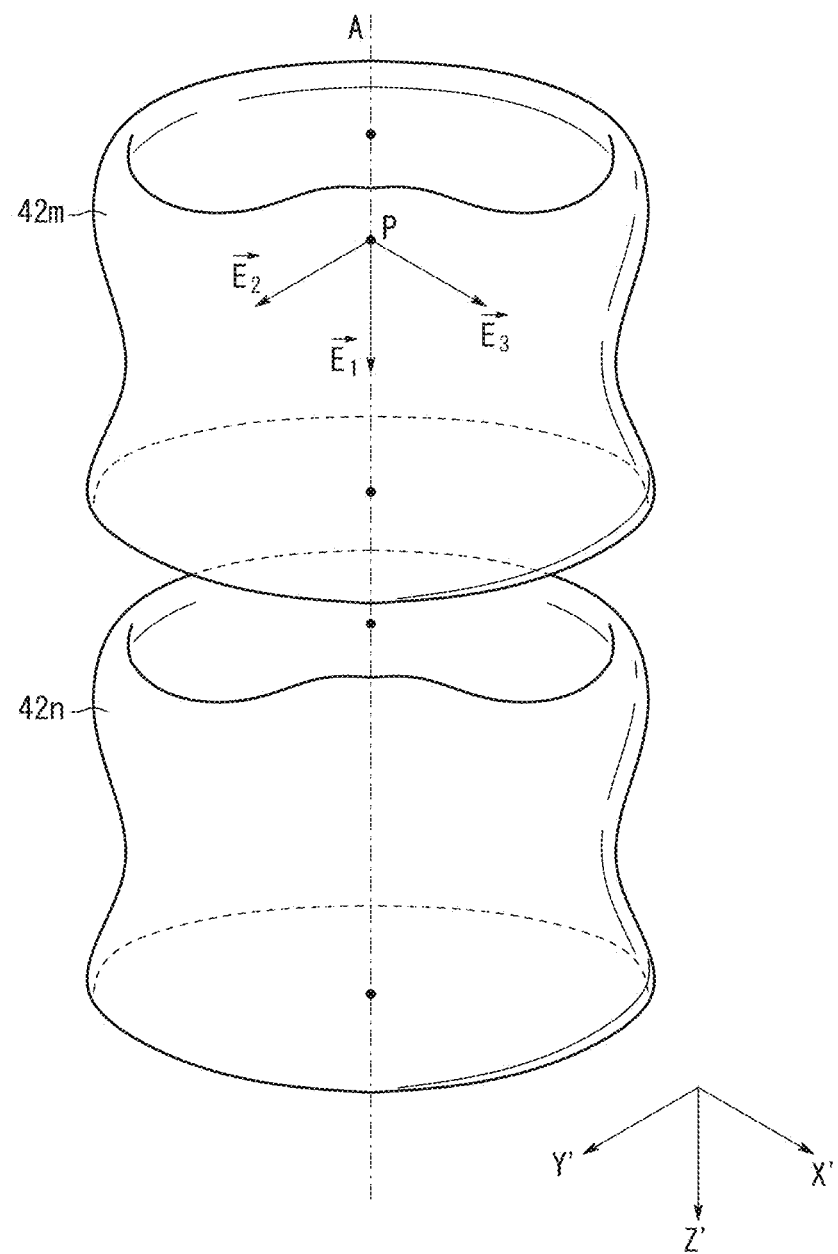
FIG. 5 is a perspective view showing a corresponding relationship between the three-dimensional shape of a vertebra and inherent vectors of a Hessian matrix at an internal point in the vertebra.

FIG. 5 is a perspective view showing a correspondence relationship between the three-dimensional shape of the vertebra 42m and inherent vectors of a Hessian matrix at an internal point P in the vertebra 42m. An inherent vector $E_1$, which corresponds to a minimum inherent value $\lambda_1$ of the Hessian matrix, is oriented along the direction (Z'-axis) in which the vertebra 42m extends. As can be understood from the configuration of the integrand represented by equation (2), the second feature quantity is extracted as representing a flat shape free of any density gradient with respect to the point P, or in particular, a vector component along the Z'-axis. In other words, the second feature quantity serves to extract a tubular pattern that extends along the Z'-axis.

Then, in step S6, the third feature quantity calculator 30 calculates a third feature quantity based on the first feature quantity calculated in step S4 and the second feature quantity calculated in step S5. The third feature quantity is expressed by the following equation (3):

$$f_3(z') = f_1(z') + \max_{\sigma \in [\sigma_0, \sigma_1]} \left[ \frac{d^2 G(z', \sigma)}{dz'^2} \otimes f_2(z') \right] \quad (3)$$

where $\alpha$ represents an arbitrary weighting coefficient, and $G(z', \sigma)$ represents a Gaussian function with a standard deviation $\sigma$.

Figure 6A:
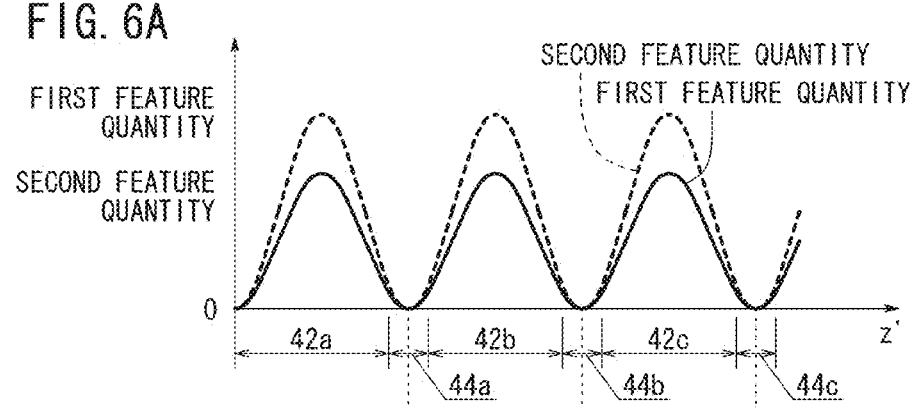
FIG. 6A is a graph showing profiles of first and second feature quantities along a Z'-axis direction.
Figure 6B:
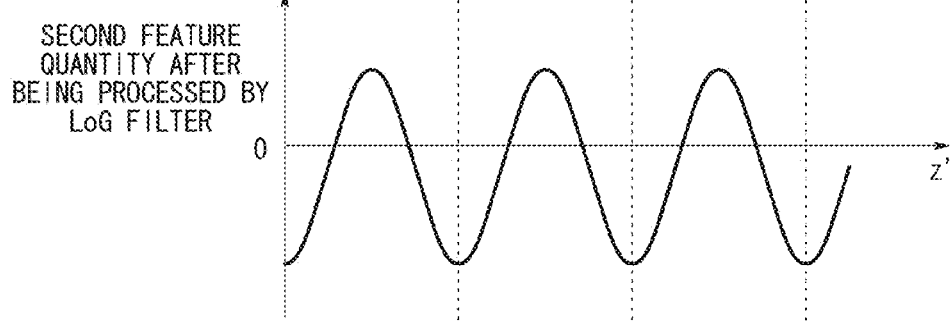
FIG. 6B is a graph showing a profile drawn after a LoG filter has acted on the second feature quantity.
Figure 6C:
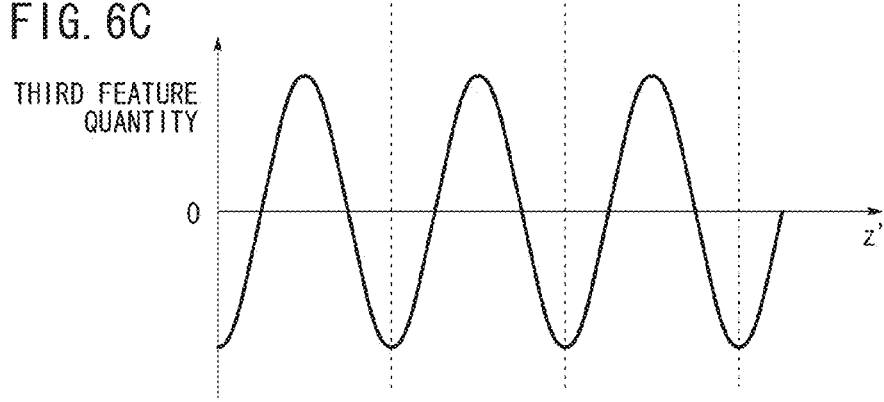
FIG. 6C is a graph showing the profile of a third quantity along the Z'-axis direction.

FIGS. 6A through 6C are graphs showing profiles of the first through third feature quantities along the Z'-axis direction.

FIG. 6A shows profiles of the first and second feature quantities along the Z'-axis direction. Profiles of the first feature quantity, indicated by the solid-line curve, and of the second feature quantity, indicated by the broken-line curve, assume a maximum value at a central position of the vertebra 42, i.e., at the sectional position T1 in FIG. 2, and a minimum value at the intervertebral disc 44, i.e., at the sectional position T2 in FIG. 2.

FIG. 6B shows a profile drawn after the LoG filter has acted on the second feature quantity. Since locations where second-order differentials are zero are extracted from the profile of the second feature quantity (see FIG. 6A), the profile shown in FIG. 6B has a periodic pattern. The profile assumes a maximum value at a central position of the vertebra 42, i.e., at the sectional position T1 in FIG. 2, and a minimum value at the intervertebral disc 44, i.e., at the sectional position T2 shown in FIG. 2.

The profile shown in FIG. 6B varies in shape depending on the value of the standard deviation $\sigma$ in the Gaussian function $G(z', \sigma)$. In the present embodiment, the value of the standard deviation $\sigma$ where the profile is maximum within a given range from $\sigma_0$ to $\sigma_1$ is selected.

FIG. 6C shows the profile of the third feature quantity along the Z'-axis direction. The third feature quantity represents a sum of the first feature quantity $f_1(z')$ and the feature quantity produced when the LoG filter acts on the second feature quantity $f_2(z')$.

In this manner, the third feature quantity $f_3(z')$ is generated so as to represent the regularity of the array of the vertebrae 42. The profile of the third feature quantity assumes a maximum value at a central position of the vertebra 42, i.e., at the sectional position T1 in FIG. 2, and assumes a minimum value at the intervertebral disc 44, i.e., at the sectional position T2 in FIG. 2.

Then, in step S7, the function matcher 32 matches the third feature quantity calculated in step S6 to a prescribed function. A matching process, which is carried out by the function matcher 32, will be described in detail below with reference to the flowchart shown in FIG. 7.

First, in step S71, the function matcher 32 sets the functional form of a matching function. If there are a plurality of functional forms, then the function matcher 32 acquires information concerning such functional forms.

As shown in FIG. 2, the vertebral group 40 has a structural feature such that the vertebral group 40 comprises an alternate array of vertebrae 42 and intervertebral discs 44. Therefore, a periodic function, such as a trigonometric function, for example, can be used as the matching function.

The vertebral group 40 also has a structural feature, such that the axial height of the vertebrae 42 becomes progressively greater from the cervical vertebrae (vertebra 42a) toward the lumbar vertebrae (vertebra 42o). A quasi-periodic function g(z') expressed by the following equation (4) may be used as a matching function:

$$g(z') = \sin\left\{\frac{2\pi(z'-c_1)}{c_2 z' + c_3}\right\} \quad (4)$$

where $c_1$ through $c_3$ represent constants for determining the form of g(z'). Assuming that $c_2=0$, g(z') is a periodic function.

The definition of the value of g(z') is in agreement with the definition of the value of the third feature quantity $f_3(z')$. In other words, the periodic function g(z') assumes a maximum value at a central position of the vertebra 42, i.e., at the sectional position T1 shown in FIG. 2, and a minimum value at the intervertebral disc 44, i.e., at the sectional position T2 shown in FIG. 2.

Then, in step S72, the function matcher 32 globally matches the third feature quantity. More specifically, the term "globally matching" implies matching the third feature quantity within an entire range of values, which can be taken by positions z' on the Z'-axes.

The function matcher 32 is capable of determining optimum constants $c_1$ through $c_3$ by performing a multivariable analysis, such as a least squares method. For example, an evaluation value $V_1$ is expressed by the following equation (5):

$$V_1(c_1, c_2, c_3) = \sum_{i=1}^{N} f_3(z'_i) \sin\left\{\frac{2\pi(z'_i - c_1)}{c_2 z'_i + c_3}\right\} \quad (5)$$

Constants $c_1$ through $c_3$ are selected, which make the evaluation value $V_1$ maximum. More specifically, a range of values that can be used for the constants $c_1$ through $c_3$ is determined in advance, and the maximum evaluation value $V_1$ is sought from all combinations of the constants $c_1$ through $c_3$ within the range.

FIG. 8 is a graph showing the matched result of the third feature quantity. In FIG. 8, the horizontal axis represents positions z' on the Z'-axes, and the vertical axis represents the third feature quantity. According to equation (4), the function matcher 32 can match the third feature quantity, which is calculated from the second tomographic images by the third feature quantity calculator 30, to the matching function.

The value of α in equation (3) should preferably be adjusted in order that the average value of the third feature quantity $f_3(z')$ becomes nil. In this case, the evaluation value $V_1$ calculated according to equation (5) corresponds to a correlative coefficient value.

To provide better matching accuracy, it is preferable to keep the third feature quantity and the amplitude of the matching function in substantial agreement with each other depending on the position z' on the Z'-axis.

Then, in step S73 shown in FIG. 7, the phase determiner 34 locally matches the third feature quantity using the three constants $c_1$ through $c_3$ selected in step S72. In particular, the term "locally matching" implies matching the third feature quantity for each of the positions z' on the Z'-axes, based on the globally matched third feature quantity. More specifically, the term of the phase δ(z') is introduced into the matching function according to equation (4) for each of the positions z', thereby optimizing the third feature quantity.

The phase determiner 34 can determine an optimum constant δ(z') by performing a multivariable analysis, such as a least squares method. For example, an evaluation value $V_2$ is expressed by the following equation (6):

$$V_2\{\delta(z')\} = \sum_{i=1}^{N} f_3(z'_i) \sin\left\{\frac{2\pi(z'_i - c_1)}{c_2 z'_i + c_3} \delta(z')\right\} \quad (6)$$

A phase δ(z') that maximizes the evaluation value $V_2$ is determined. In the present embodiment, phases are determined as discrete values $\delta_1, \delta_2, \ldots$ successively according to a dynamic programming process, and the phase δ(z') ultimately is determined within an entire range from $\delta_1$ to $\delta_N$.

Figure 9A:
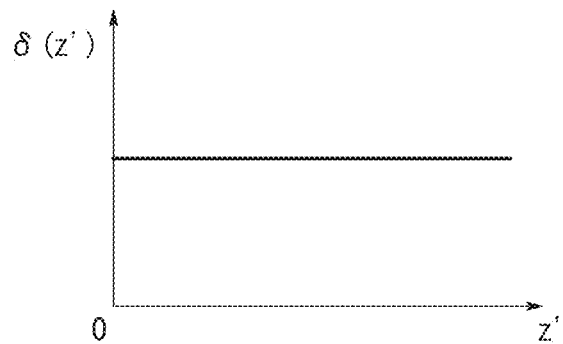
FIGS. 9A and 9B are graphs showing determined phases.
Figure 9B:
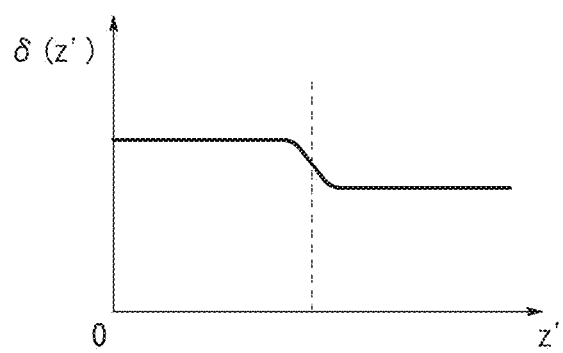

FIGS. 9A and 9B are graphs showing determined phases. In each of FIGS. 9A and 9B, the horizontal axis represents positions z' on the Z'-axes, and the vertical axis represents the phase δ(z').

FIG. 9A shows the determined phase δ(z') for a typical vertebral group 40. Since the vertebrae 42 are arranged regularly, the process of global matching (step S72) alone provides sufficient matching accuracy. The phase δ(z') is constant irrespective of the positions z'.

FIG. 9B shows the determined phase δ(z') for a vertebral group 40 in which a certain vertebra 42 thereof is broken. Regularity of the vertebrae 42 is disrupted at the broken position, as a boundary point between the left side region (upper side region) and the right side region (lower side region). Therefore, as shown in FIG. 9B, the phase δ(z') becomes discrete at the broken position, which forms the boundary point. At the left (or right) side region of the broken position, since regularity of the vertebrae 42 is not lost, the phase δ(z') is constant irrespective of the positions z'.

Since the function can be matched in view of the local positional displacement of a vertebra 42, the accuracy at which the position of each of the vertebrae 42 is estimated is increased.

Referring back to FIG. 3, in step S8, the vertebral position estimator 36 estimates the position of each of the vertebrae 42 on the Z'-axes.

More specifically, the vertebral position estimator 36 estimates the position of each of the vertebrae 42 based on a matching function, to which the third feature quantity is matched. For example, based on the matching function according to equation (4), the nth intervertebral disc 44 is determined according to the following equation (7):

$$z'(n) = \frac{2c_1 + (2n+1)c_3}{2 - (2n+1)c_2} \quad (7)$$

Equation (7) represents a position in view of the globally matched result only. Further in view of the locally matched result, an nth intervertebral disc 44 is determined approximately according to the following equation (8) where δ(Z') is a first-order infinitesimal:

$$z'(n) = \frac{2c_1 + (2n+1)c_3}{2 - (2n+1)c_2} + \delta\left(\frac{2c_1 + (2n+1)c_3}{2 - (2n+1)c_2}\right) \quad (8)$$

Then, in step S9, the vertebral position estimator 36 converts the position of each of the vertebrae 42 into a position on the Z-axis. More specifically, the vertebral position estimator 36 converts the position of each of the vertebrae 42 on the Z'-axis estimated in step S8 into a position in the XYZ coordinate system. Such a coordinate transformation can be performed easily, because the positional relationship between points P on the Z'-axes and coordinates in the XYZ coordinate system is already known.

Finally, in step S10 (first allocating step), the identifying information allocator 37 allocates identifying information to the partitioned and recognized vertebrae 42.

In the present embodiment, anatomical types of vertebrae 42 are used as identifying information. More specifically, vertebrae 42 of the spine (vertebral group 40) are classified into first through seventh cervical vertebrae, first through twelfth thoracic vertebrae, first through fifth lumbar vertebrae, first through fifth sacral vertebrae (sacral bones), and a small number of caudal vertebrae (coccygeal bones).

Figure 10:
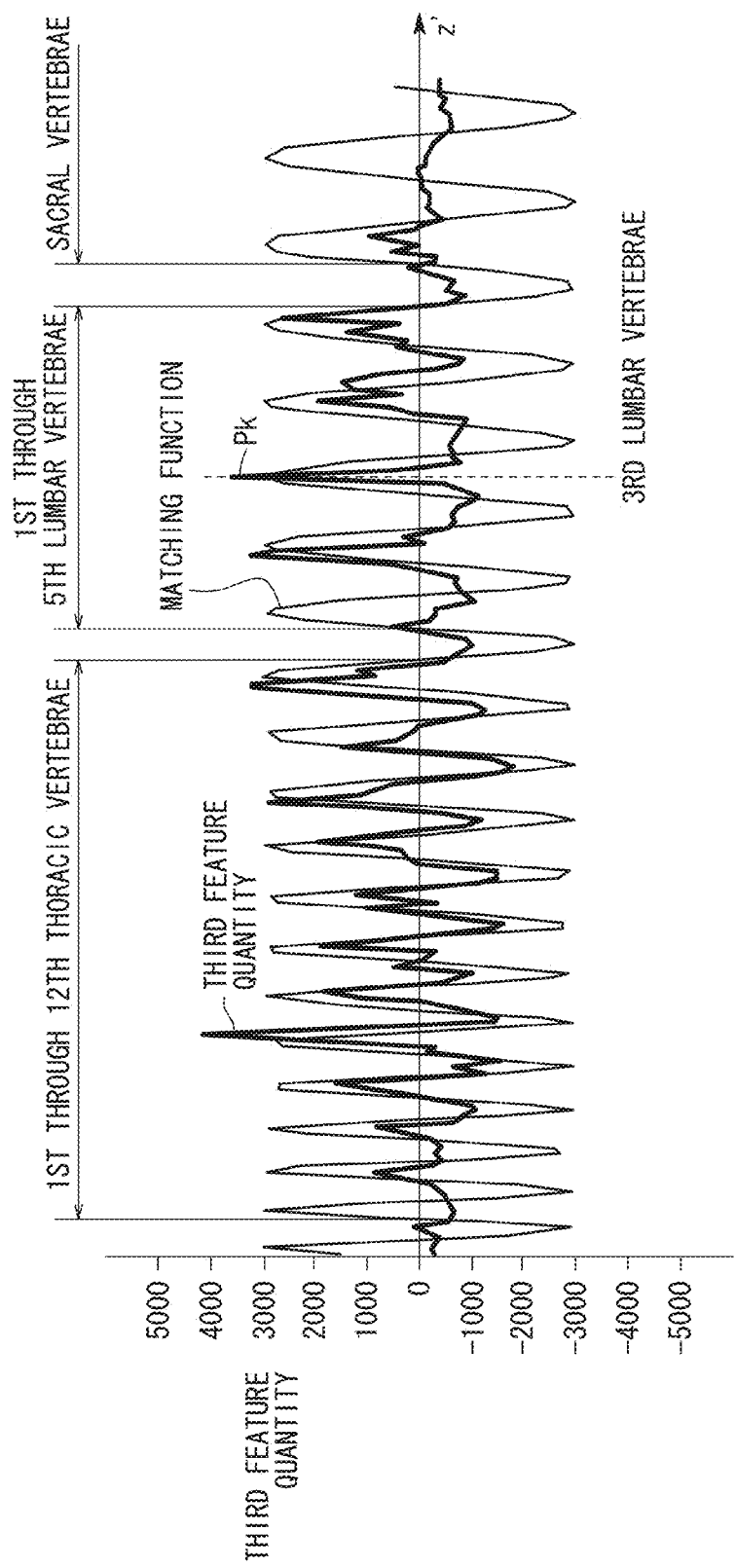
FIG. 10 is a graph similar to FIG. 8, which is combined with corresponding positions of thoracic vertebrae, lumbar vertebrae, and sacral vertebrae.

FIG. 10 is a graph similar to FIG. 8, which is combined with corresponding positions of thoracic vertebrae, lumbar vertebrae, and sacral vertebrae. In FIG. 10, the horizontal axis represents positions z' on the Z'-axes, and the vertical axis represents the third feature quantity (see FIG. 8).

The identifying information allocator 37 allocates identifying information "third lumbar vertebra" to a vertebra 42 at a certain peak Pk, in response to an instruction entered from an external circuit. At this time, the identifying information allocator 37 acquires table data containing an association between the vertebrae 42 and types of the vertebrae 42 from the memory 18. The instruction may be a manual instruction entered by a doctor or a technologist (hereinafter referred to as "user") through an input device (not shown), or an automatic instruction, which is generated based on the result of an image recognition process performed by the vertebra segmentation apparatus 10.

The identifying information allocator 37 identifies vertebrae 42, which correspond to five peaks including the peak Pk, two peaks preceding the peak Pk, and two peaks following the peak Pk, as the five lumbar vertebrae. More specifically, the identifying information allocator 37 refers to the table data, and allocates identifying information "first through fifth lumbar vertebrae" (except the third lumbar vertebra) to each of the identified vertebrae 42 corresponding to the peaks, successively in an ascending order of the positions z'.

The identifying information allocator 37 also identifies vertebrae 42, which correspond to twelve peaks that are positioned leftwardly (in a negative Z'-axis direction) of the peak corresponding to the first lumbar vertebra, as twelve thoracic vertebrae. More specifically, the identifying information allocator 37 refers to the table data, and allocates identifying information "first through twelfth thoracic vertebrae" to each of the identified vertebrae 42 corresponding to the peaks successively, in an ascending order of the positions z'.

The identifying information allocator 37 also identifies vertebrae 42, which correspond to five peaks that are positioned rightwardly (in a positive Z'-axis direction) of the peak corresponding to the fifth lumbar vertebra, as five sacral vertebrae. More specifically, the identifying information allocator 37 refers to the table data, and allocates identifying information "first through fifth sacral vertebrae" to each of the identified vertebrae 42 corresponding to the peaks, successively in an ascending order of the positions z'.

Thereafter, the identifying information allocator 37 identifies peaks corresponding to cervical vertebrae or caudal vertebrae, and allocates identifying information, in accordance with the description of the table data, to the vertebrae 42 corresponding to the identified peaks.

In this manner, the identifying information allocator 37 allocates identifying information to the vertebrae 42 in step S10. The identifying information allocator 37 may also allocate identifying numbers to the intervertebral discs 44, which are interposed between the vertebrae 42, in the same manner as with the vertebrae 42.

The seventh cervical vertebra and a different name therefor, e.g. "prominent vertebra", may be associated with each other, so that the user may be able to select which one of these terms should be used.

Furthermore, inherent vertebral numbers may be allocated to the vertebrae 42 in an order from the highest vertebra, i.e., the first cervical vertebra, to the lowest vertebra. Identifying information may be allocated successively from the highest vertebra, i.e., the first cervical vertebra, or from the lowest vertebra, i.e., the fifth sacral vertebra.

Thereafter, when the medical image is displayed on a display device (not shown), the identifying information, which is output to the output unit 16, may be converted into visible information and displayed together with the medical image. The identifying information may be converted into visible information according to any of various known image displaying techniques.

FIG. 11 is a view showing an example of a sagittal tomographic image of lumbar vertebrae. As shown in FIG. 11, strings of characters, signifying first through fifth lumbar vertebrae, may be displayed over a tomographic image 100 at respective positions corresponding to vertebrae 42 to which the identifying information "first through fifth lumbar vertebrae" have been allocated. By observing the displayed strings of characters, the user is able to immediately recognize the anatomical type (name) of the displayed vertebrae 42 for diagnostic purposes.

As described above, tomographic images of a subject are generated at intervals along a central line A (Z'-axes) of the vertebrae 42. Then, based on the generated tomographic images, first and second feature quantities representative of the clearness of sectional shapes both transverse and parallel to the Z'-axes at the vertebrae 42 are calculated with respect to each of points on the Z'-axes. Then, based on the calculated first and second feature quantities, a third feature quantity representative of the regularity of the array of the vertebrae 42 is calculated with respect to each of the points on the Z'-axes. Then, the position of each of the vertebrae 42 on the Z'-axes is estimated based on the calculated third feature quantity. Accordingly, it is possible to perform a quantitative density analysis based on cross-sectional shapes viewed from two different directions, thereby allowing the vertebrae 42 to be partitioned and recognized in a three-dimensional medical image of the subject whose spinal shape is deformed entirely or locally. This process is particularly effective in analyzing a medical image of the spine, which is deformed in its entirety due to spinal curvature.

The prescribed periodic function or quasi-periodic function includes a phase as a variable. Preferably, the phase should be determined successively with respect to each point along the central axis, according to a dynamic programming process. It is thus possible to reduce errors in matching the third feature quantity to the matching function, for thereby estimating the position of each vertebra 42 with high accuracy. This process is particularly effective in analyzing a medical image of the spine, which is deformed locally due to a bone fracture.

The vertebra segmentation method according to the present embodiment is useful in clinical applications. For example, a partitioned image of the vertebrae 42, which was acquired from a subject in the past, and a partitioned image of the vertebrae 42, which is acquired from the same subject at present, can be compared with each other to discover chronological changes in the shape of the subject's spine. The vertebra segmentation method also is useful as a tool for assisting in diagnosing, i.e., preventing, checking, treating, and monitoring, spinal disorders including spinal curvature.

Operations of the vertebra segmentation apparatus 10, for comparing partitioned images of the vertebrae 42 at different times with each other, will be described in detail below with reference to FIGS. 1, 3, and 12.

Figure 3:
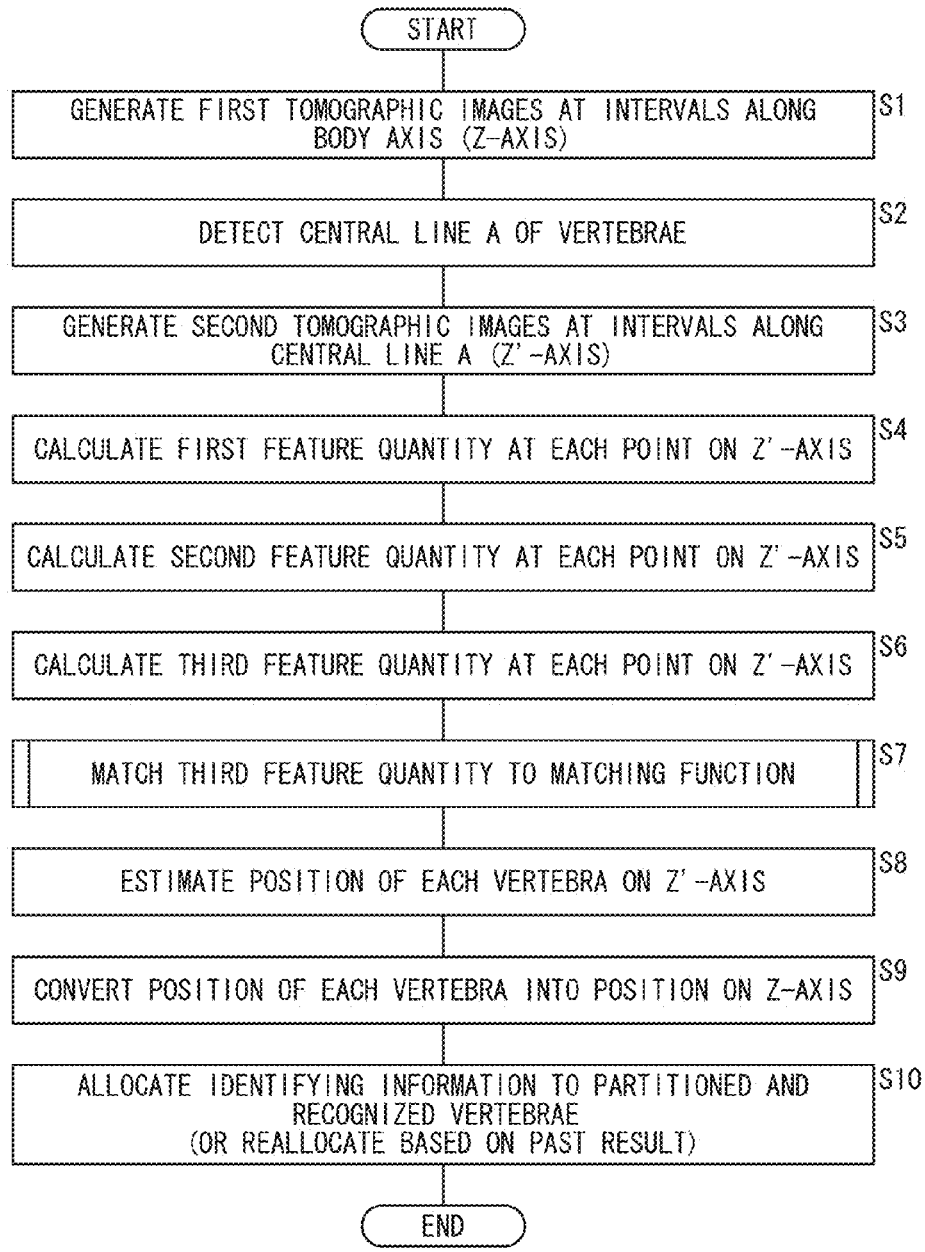
FIG. 3 is a flowchart of an operation sequence of the vertebra segmentation apparatus.

At the first time t1, e.g., in the past, the vertebrae 42 are partitioned and recognized in steps S1 through S9, and processing for allocating the identifying information in step S10 are carried out according to the flowchart shown in FIG. 3. The memory 18 records therein positional information of the vertebrae 42, together with identifying information associated with such positional information. Alternatively, the positional information and the identifying information may be recorded in an external device, such as a database server or the like, for example.

At the second time t2, e.g., at present, the vertebrae 42 are partitioned and recognized in steps S1 through S9, according to the flowchart shown in FIG. 3. It is preferable to perform the process, which takes place at the second time t2, under the same conditions as the process carried out at the first time t1. In particular, it is preferable to normalize a distribution of pixel values prior to acquisition of a three-dimensional medical image, so that the vertebrae 42 can be partitioned and recognized with high reproducibility by the controller 14.

Then, the feature quantity determiner 38 checks the third feature quantity calculated at the first time t1 and the third feature quantity calculated at the second time t2 against each other. An example, in which the shape of the spine (vertebral group 40) of the subject has not changed significantly between the first time t1 and the second time t2, will be described below.

In FIG. 12, the upper graph shows a profile (hereinafter referred to as "profile $f_A(z')$") of the third feature quantity calculated from the acquired image at the first time t1. In FIG. 12, the lower graph shows a profile (hereinafter referred to as "profile $f_B(z')$") of the third feature quantity calculated from the acquired image at the second time t2. As shown in FIG. 12, the profile $f_A(z')$ and the profile $f_B(z')$ exhibit substantially the same tendency, except that the profile $f_B(z')$ is shifted from the profile $f_A(z')$ in its entirety along the positive Z'-axis direction by a shift amount $\Delta z'$.

The feature quantity determiner 38 performs a matching process on the profile $f_A(z')$ and the profile $f_B(z')$. More specifically, the feature quantity determiner 38 calculates the shift amount $\Delta z'$ in order to minimize the Sum of Square Difference (SSD) between the profile $f_A(z')$ and the profile $f_B(z'-\Delta z')$. The evaluation function of the matching process may be a known function, such as a Normalized Cross Correlation (NCC), a Sum of Absolute Difference (SAD), or the like, as well as SSD. Alternatively, peak values of the profiles of the third feature quantities may be compared with each other.

The feature quantity determiner 38 then determines whether or not characteristics of the profile $f_A(z')$ agree with characteristics of the profile $f_B(z')$. Alternatively, the feature quantity determiner 38 may determine whether or not the profile $f_A(z')$ and the profile $f_B(z'-\Delta z')$ are sufficiently approximate to each other, or whether or not a correlative coefficient thereof exceeds a certain threshold value. If the feature quantity determiner 38 judges that characteristics of the profile $f_A(z')$ agree with characteristics of the profile $f_B(z')$, then the feature quantity determiner 38 supplies the shift amount $\Delta z'$ to the memory 18.

Then, in step S10 (second allocating step), the identifying information allocator 37 allocates the same identifying information as the identifying information allocated at the first time t1. Based on the checked result from the feature quantity determiner 38, the identifying information allocator 37 identifies peaks at a second time t2, which correspond to peaks at the first time t1. The identifying information allocator 37 then allocates, or reallocates, the same identifying information as the identifying information at the first time t1 to the vertebrae 42 that correspond to the identified peaks. Upon allocating, or reallocating, the identifying information, the identifying information allocator 37 refers to the positional information of the vertebrae 42 at the time t1, the positional information of the vertebrae 42 at the time t2, the shift amount $\Delta z'$, and the table data from the memory 18.

In FIG. 12, the first time t1 is in the past, whereas the second time t2 takes place at the present (t1<t2). However, the first time t1 may take place at the present, and the second time t2 may be in the past (t1>t2).

Since, as described above, the predefined identifying information (e.g., anatomical types of vertebrae 42) is allocated to the vertebrae 42 at estimated positions on the Z'-axes, the user, who is a medical professional, finds it easy to identify the vertebrae 42.

Since the identifying information, which is allocated at the first time t1, is allocated to the vertebrae 42 at positions on the Z'-axes estimated at the second time t2, it is easy to discover chronological changes in the shape of the spine of the subject.

The subject, whose images are processed by the vertebra segmentation apparatus 10 according to the present invention, is not limited to a human being, but may be any of various vertebrate animals.

Although a certain preferred embodiment of the present invention has been shown and described in detail, it should be understood that various changes and modifications may be made to the embodiment without departing from the scope of the invention as set forth in the appended claims.

What is claimed is:

1. A vertebra segmentation apparatus comprising:
an image generator constructed and arranged to generate tomographic images at intervals along central axes of respective vertebrae;
a first feature quantity calculator constructed and arranged to calculate a first feature quantity representative of a clearness of sectional shapes crossing the central axis at the vertebrae, for each of respective points on the central axis, based on the tomographic images generated by the image generator;
a second feature quantity calculator constructed and arranged to calculate a second feature quantity representative of a clearness of sectional shapes parallel to the central axis at the vertebrae, for each of the respective points on the central axis, based on the tomographic images generated by the image generator;
a third feature quantity calculator constructed and arranged to calculate a third feature quantity representative of a regularity of an array of the vertebrae, for each of the respective points on the central axis, based on the first feature quantity calculated by the first feature quantity calculator and the second feature quantity calculated by the second feature quantity calculator; and
a vertebral position estimator constructed and arranged to estimate positions of the vertebrae on the central axis based on the third feature quantity, which is calculated by the third feature quantity calculator, for each of the respective points on the central axis.

2. A vertebra segmentation apparatus according to claim 1, wherein the first feature quantity comprises a feature quantity for extracting an annular pattern around each of the respective points on the central axis.

3. A vertebra segmentation apparatus according to claim 1, wherein the second feature quantity comprises a feature quantity for extracting a tubular pattern extending along the central axis.

4. A vertebra segmentation apparatus according to claim 1, further comprising:
a function matcher constructed and arranged to match the third feature quantity calculated for each of the respective points on the central axis to a prescribed periodic function or a quasi-periodic function,
wherein the vertebral position estimator is constructed and arranged to estimate the positions of the vertebrae on the central axis based on the prescribed periodic function or the quasi-periodic function matched by the function matcher.

5. A vertebra segmentation apparatus according to claim 4, wherein the prescribed periodic function or the quasi-periodic function includes a phase as a variable, and further comprising:
a phase determiner constructed and arranged to determine the phase successively for the points on the central axis.

6. A vertebra segmentation apparatus according to claim 1, further comprising:
an identifying information allocator constructed and arranged to allocate predefined identifying information to each of the vertebrae depending on the position thereof on the central axis, which is estimated by the vertebral position estimator.

7. A vertebra segmentation apparatus according to claim 6, wherein the identifying information allocator is constructed and arranged to allocate identifying information, which is the same as the identifying information allocated based on the tomographic image generated at a first time, to each of the vertebrae depending on the position thereof on the central axis, which is estimated based on the tomographic image generated at a second time.

8. A vertebra segmentation apparatus according to claim 7, further comprising:
a feature quantity determiner constructed and arranged to determine whether or not characteristics of the third feature quantity calculated based on the tomographic image generated at the first time agree with characteristics of the third feature quantity calculated based on the tomographic image generated at the second time,
wherein the identifying information allocator is constructed and arranged to allocate the identifying information, which is the same as the first-mentioned identifying information, if the feature quantity determiner determines that the characteristics of the third feature quantities agree with each other.

9. A vertebra segmentation apparatus according to claim 6, wherein the identifying information represents anatomical types of the vertebrae.

10. A vertebra segmentation method comprising the steps of:
generating, by a processing unit, tomographic images at intervals along central axes of respective vertebrae;
calculating, by the processing unit, a first feature quantity representative of a clearness of sectional shapes crossing the central axis at the vertebrae, for each of respective points on the central axis, based on the generated tomographic images;
calculating, by the processing unit, a second feature quantity representative of a clearness of sectional shapes parallel to the central axis at the vertebrae, for each of the respective points on the central axis, based on the generated tomographic images;
calculating, by the processing unit, a third feature quantity representative of a regularity of an array of the vertebrae, for each of the respective points on the central axis, based on the calculated first feature quantity and the calculated second feature quantity; and
estimating, by the processing unit, positions of the vertebrae on the central axis based on the third feature quantity, which is calculated for each of the respective points on the central axis.

11. A non-transitory recording medium storing therein a program that, when executed on a computer directs the computer to perform a method of partitioning and recognizing a plurality of vertebrae from a three-dimensional medical image that includes the vertebrae, the method comprising:
generating tomographic images at intervals along central axes of respective vertebrae;
calculating a first feature quantity representative of a clearness of sectional shapes crossing the central axis at the vertebrae, for each of respective points on the central axis, based on the generated tomographic images;
calculating a second feature quantity representative of a clearness of sectional shapes parallel to the central axis at the vertebrae, for each of the respective points on the central axis, based on the generated tomographic images;
calculating a third feature quantity representative of a regularity of an array of the vertebrae, for each of the respective points on the central axis, based on the calculated first feature quantity and the calculated second feature quantity; and
estimating positions of the vertebrae on the central axis based on the third feature quantity, which is calculated for each of the respective points on the central axis.

* * * * *